United States Patent [19]

Ghisalba et al.

[11] Patent Number: 4,492,756
[45] Date of Patent: Jan. 8, 1985

[54] MICROORGANISMS OF THE GENUS HYPHOMICROBIUM AND PROCESS FOR DEGRADING COMPOUNDS WICH CONTAIN METHYL GROUPS IN AQUEOUS SOLUTIONS

[75] Inventors: Oreste Ghisalba, Basel; Franz Heinzer, Porrentruy; Martin Küenzi, Muttenz, all of Switzerland

[73] Assignee: Ciba-Geigy Corporation, Ardsley, N.Y.

[21] Appl. No.: 445,783

[22] Filed: Dec. 1, 1982

[30] Foreign Application Priority Data

Dec. 11, 1981 [CH] Switzerland ............ 7932/81

[51] Int. Cl.$^3$ ............ C12N 1/20; C12N 1/32; C07 00/00; C12R 1/01
[52] U.S. Cl. ............ 435/253; 435/247; 435/262; 435/822; 210/611; 426/61
[58] Field of Search ............ 435/253, 247, 262; 210/611

[56] References Cited

U.S. PATENT DOCUMENTS 4,317,843 3/1982 MacLennan et al. .......... 435/247 X

OTHER PUBLICATIONS

Attwood et al., J. of General Microbiology, vol. 84 pp. 350–356 (1974)–and Chem. Abstracts summary item 53966u.
Chem. Abstracts, vol. 85, No. 23 item 85:174019h.
Chem. Abstracts, vol. 82, No. 9 item 53953n.

*Primary Examiner*—Lionel M. Shapiro
*Attorney, Agent, or Firm*—Michael W. Glynn

[57] ABSTRACT

The present invention relates to novel facultative methylotrophic microorganisms of the genus Hyphomicrobium, to protein-containing biomass, and to a process for the microbiological purification of aqueous solutions, e.g. wastewaters, which contain methanol, ethanol, glucose, dimethyl phosphite, trimethyl phosphite, sodium formate, sodium acetate, methylammonium chloride, dimethylammonium chloride, ethylmethylammonium chloride or, chiefly, sodium methyl sulfate, as pollutants. The respective microorganism is cultured in aqueous solution and the pollutant is degraded simultaneously.

7 Claims, No Drawings

MICROORGANISMS OF THE GENUS HYPHOMICROBIUM AND PROCESS FOR DEGRADING COMPOUNDS WICH CONTAIN METHYL GROUPS IN AQUEOUS SOLUTIONS

The present invention relates to novel facultative methylotrophic microorganisms of the genus Hyphomicrobium, to a process for the microbiological purification of aqueous solutions by degrading compounds which contain methyl groups in the presence of said microorganisms, to the biomass which is produced by said microorganisms, and to the use of the biomass obtained by the process of this invention.

The term "methylotrophic microorganisms" shall be understood as meaning those microorganisms which grow on nutrient media containing, as carbon source, compounds having only one carbon atom, e.g. methanol.

The term "facultative methylotrophic microorganisms" shall be understood as meaning those microorganisms which grow on nutrient media containing, as carbon source, compounds having one carbon atom, e.g. methanol, and/or compounds having several carbon atoms, e.g. glucose.

There are described in the literature methylotrophic microorganisms which, in aqueous solution, are able to degrade or to utilise as carbon source, or as carbon and nitrogen source, one or more compounds selected from the group of organic compounds consisting of: methanol, ethanol, acetates, e.g. sodium acetate, formates, e.g. sodium formate, monosaccharides, e.g. glucose, disaccharides, e.g. saccharose, dimethyl phosphite, trimethyl phosphite or specific methylammonium compounds, e.g. methylammonium chloride, ethylmethylammonium chloride, or dimethylammonium chloride, and the free amines thereof.

Such microorganisms are deposited in various culture collections, e.g. in the American Type Culture Collection (ATCC), in the Deutsche Sammlung von Microorganismen (DSM), or in the National Collection of Industrial Bacteria (NCIB), and listed in the catalogues published by these collections.

Large-scale production in the chemical industry gives rise to the formation of aqueous solutions, e.g. wastewaters, which contain these compounds and/or methyl sulfates, e.g. sodium methyl sulfate, as pollutants, in some cases in very high concentrations. In order to prevent these compounds (salts) from becoming an environmental nuisance, such wastewaters have to be purified. However, purification creates very serious problems. For example, lower alkylammonium salts, e.g. methylammonium chloride, ethylmethylammonium chloride or dimethylammonium chloride, have up to now been eliminated by incineration. In general, the incineration of organic waste must be regarded in the long term as a very unsatisfactory method of elimination which incurs high costs and also creates severe environmental problems.

This problem is solved by the present invention, which relates to novel facultative methylotrophic microorganisms of the genus Hyphomicrobium, which microorganisms are able to degrade all the above mentioned organic compounds and, in particular, methyl sulfates, e.g. sodium methyl sulfate. The invention also relates to a process for the microbiological purification of aqueous solutions by degradation of lower alkanols, lower alkanoates, monosaccharides, disaccharides, dimethyl phosphite, trimethyl phosphite, lower alkylammonium compounds or of free amines thereof, or of methyl sulfate compounds or mixtures of said compounds, in the presence of these microorganisms. The invention further relates to the biomass which is prepared from these microorganisms and to the use of said biomass obtainable by the process of this invention.

Throughout this specification, the definitions of compounds generally employed preferably have the following meanings: lower alkanols are e.g. methanol or ethanol; lower alkanoates are e.g. salts of formic or acetic acid, e.g. sodium formate, sodium acetate or potassium acetate; monosaccharides are e.g. hexoses, e.g. glucose, and also fructose, mannose or galactose; disaccharides are e.g. saccharose, maltose or lactose; lower alkylammonium compounds are e.g. methylammonium chloride, dimethylammonium chloride or ethylmethylammonium chloride; methyl sulfate compounds are e.g. sodium or potassium methyl sulfate.

The present invention relates in particular to microorganisms of the genus Hyphomicrobium and to a process for the microbiological purification of aqueous solutions by degradation of methanol, ethanol, glucose, dimethyl phosphite, trimethyl phosphite, sodium formate, sodium acetate, methylammonium chloride, dimethylammonium chloride or ethylmethylammonium chloride, or of free amines corresponding to these salts, or of sodium methyl sulfate.

Most particularly, the present invention relates to microorganisms of the genus Hyphomicrobium selected from the group of the following strains: Hyphomicrobium MS 72 (NRRL-B-12573), MS 75 (NRRL-B-12572), MS 219 (NRRL-B-12571), MS 223 (NRRL-B-12570) and MS 246 (NRRL-B-12569), and to a process for the microbiological purification of aqueous solutions by degradation of sodium methyl sulfate.

The novel strains were deposited with the Agricultural Research Culture Collection (NRRL) in Peoria, Ill. 61604, U.S.A., on Nov. 3rd, 1981 under the Budapest Treaty on the International Recognition of the Deposit of Microorganisms for the purposes of patent procedure and are kept there under the desposit numbers specified in Table 1.

ISOLATION OF THE NOVEL MICROORGANISMS

The novel microorganisms originate from the sludge of a wastewater purification plant of Ciba-Geigy AG (WPP-CG) and from a waste tip in Croglio, Canton Ticino, Switzerland, and have been isolated in a manner known per se as follows:

METHOD 1

A sample of wastewater or a sludge suspension (1 g per 10 ml of sterile water) is plated out on sterile agar (based on MV 7 nutrient solution) which contains sodium methyl sulfate. The MV 7 nutrient solution contains, in one liter of water, the following ingredients: 2 g of $NH_4NO_3$ (nitrogen source), 1.4 g of $Na_2HPO_4$, 0.6 g of $KH_2PO_4$ (buffer and phosphorus source), 0.2 g of $MgSO_4.7H_2O$, 0.01 g of $CaCl_2.2H_2O$, 0.001 g of $FeSO_4.7H_2O$, and 1 ml of a trace element solution (consisting of 20 mg/l of each of $Na_2MoO_4.2H_2O$, $Na_2B_4O_7.10H_2O$, $MnSO_4.H_2O$, $ZnSO_4.H_2O$ and $CuSO_4.5H_2O$.

The salts are dissolved in distilled water, the solution is adjusted to pH 7 with dilute NaOH and made up to 1 liter with distilled water. The solid MV 7 agar culture medium is prepared by adding a further 20 g/l of agar (Difco) to the nutrient solution. Sterilisation is effected in an autoclave. Incubation is carried out at 28°–30° C. Single colonies are cautiously picked and streaked again on the same medium. This procedure is repeated a number of times until pure isolates are obtained.

METHOD 2

A sample of wastewater or a sludge suspension (1 g per 10 ml of sterile water) is put into a shaking bottle containing sterile MV 7 nutrient solution. An aqueous solution of sodium methyl sulfate which is filtered under sterile conditions is added, and the batch is incubated for 14 days at 28° C. as stationary culture or for 7 days at 250 rpm as shake culture. Then 0.5 ml of this first enrichment culture is added to the fresh MV 7 nutrient solution and again incubated at 28° C. as stationary culture or shake culture. Then 0.5 ml of this second enrichment culture is in turn added to the fresh nutrient solution and incubation is carried out for 7 days at 28° C. The second or third enrichment culture is plated out on sterile MV 7 agar which contains sodium methyl sulfate [MV 7 nutrient solution with the addition of 20 g/1 of agar (Difco)] and incubated at 28° C. Single colonies are cautiously picked and streaked again on the same medium. This procedure is repeated several times until pure isolates are obtained.

Deposit number, origin and method of isolation of each individual member of the strains listed hereinafter are indicated in Table 1.

TABLE 1

| Designation Genus | Strain No. | Deposit No. (NRRL) | Origin | Method |
| --- | --- | --- | --- | --- |
| Hyphomicrobium | MS 72 | B-12573 | WPP-CG | 1 |
| Hyphomicrobium | MS 75 | B-12572 | WPP-CG | 1 |
| Hyphomicrobium | MS 219 | B-12571 | WPP-CG | 2 |
| Hyphomicrobium | MS 223 | B-12570 | WPP-CG | 2 |
| Hyphomicrobium | MS 246 | B-12569 | Croglio | 2 |

CHARACTERISATION OF THE NOVEL MICROORGANISMS

1. General parameters and microscopy

All the strains listed in Table 1 are gram-negative, oxidasepositive, and grow best under aerobic conditions at 28° to 30° C. As sources of carbon or of carbon and nitrogen they are able to utilise methanol, ethanol, glucose, dimethyl phosphite, trimethyl phosphite, formate, acetate, methylammonium, dimethylammonium, ethylmethylammonium or methyl sulfate ions. Because of these properties, the novel microorganisms are suitable for processes for the microbiological purification of those aqueous solutions which contain these sources of carbon or of carbon and nitrogen as pollutants.

Under microscopic observation (optical microscope), all the strains are very similar and appear as motile rods about $1-2\mu$ long which occur individually or in agglomerates. Many cells have "appendages" or hyphae. The electron microscope image accords well with the findings made by optical microscopy. Some of the cells have long "appendages" or "hyphae", with each cell having at most one such polar appendage. A number of cells with appendages carry flagellae. Budding is observed at the end of the appendage in a number of cells with hyphae. Another type of cell has no appendage but has instead a subpolar flagellum.

2. Biochemical characterisation and classification of the novel microorganisms

Two commercially available assays are employed for characterising the strains listed in Table 1. Both assays are suitable for general biochemical characterisations.

(a) "Oxi/Ferm Tube" Assay (Roche)

This assay is used for gram-negative rods with positive oxidase reaction. The assay is carried out in parallel once with cells of the strain in question from methanol-agar and once from nutrient agar. The experiment is carried out in accordance with the manufacturer's instructions. The test results are set forth in Table 2.

TABLE 2

MS Stains tested with "Oxi/Ferm Tube" 48 h, 28° C.)

biochemical assay

| Strain No. | anaerobic dextrose cleavage | arginine dihydrolase | $N_2$ production | $H_2S$ formation | indole formation | xylose cleavage | aerobic dextrose cleavage | Urease | citrate utilisation |
| --- | --- | --- | --- | --- | --- | --- | --- | --- | --- |
| MS 72 | + | − | −* | − | − | + | + | + | ± |
| MS 75 | − | − | −* | − | − | − | − | − | − |
| MS 219 | − | − | + | − | − | ± | − | + | + |
| MS 223 | − | − | −* | − | − | − | − | − | − |
| MS 246 | − | − | + | − | − | ± | − | + | + |

\+ both parallel assays positive
− both parallel assays negative
± one assay positive, one assay negative (in xylose cleavage: positive for MS 219 and 246 from methanol/agar; in citrate utilisation: positive for MS 72 from nutrient agar)
*positive in the API 20E test The test results in Table 2 permit a classification of the individual strains into three groups on the basis of their common features:

TABLE 3

| Strain No. | Uniformity | Group |
| --- | --- | --- |
| MS 75 | individual strain | I |
| MS 75 and 223 | identical | II |
| MS 219 and 246 | identical | III |

(b) API 20E Assay

The assay is carried out in parallel once with cells of the relevant strain from methanol/agar and from nutrient agar. The procedure is in accordance with the manufacturer's instructions. The results are set forth in Table 4.

TABLE 4

MS Strains tested with API 20 E (48 h, 28° C.)

biochemical assay

ONPG:

IND:
TDA: tryptophane

TABLE 4-continued

| | MS Strains tested with API 20 E (48 h, 28° C.) | | | | | | | | | | | |
|---|---|---|---|---|---|---|---|---|---|---|---|---|
| Strain No. | hydrolysis by β-galactosidase | ADH: arginine dihydrolase | LDC: lysine decarboxylase | ODC: ornithine decarboxylase | CIT: citrate utilisation | H2S: thiosulfate cleavage | URE: urease | tryptophane desaminase | degradation indole formation ↓ | VP: acetoin test | GEL: gelatin liquefaction | GLU: glucose utilisation |
| MS 72 | + | − | + | + | + | − | −* | − | − | + | − | + |
| MS 75 | + | − | − | − | − | − | − | − | − | ± | + | − |
| MS 219 | + | − | ± | − | + | − | + | − | − | ± | − | − |
| MS 223 | + | − | − | − | − | − | − | − | − | ± | − | − |
| MS 246 | + | ± | − | − | + | − | + | − | − | ± | − | − |

| | biochemical assay | | | | | | | | | | |
|---|---|---|---|---|---|---|---|---|---|---|---|
| Strain No. | MAN: mannitol utilisation | INO: inositol utilisation | SOR: sorbitol utilisation | RHA: rhamnose utilisation | SAC: saccharose utilisation | MEL: melibiose utilisation | AMY: amygdaline utilisation | ARA: L-arabinose utilisation | OX: oxidase | NO2: N2: nitrate reduction | | CAT: catalase |
| MS 72 | + | + | + | + | + | + | + | + | +w | + | + | − |
| MS 75 | − | − | − | − | − | − | − | − | +w | + | + | + |
| MS 219 | − | − | − | − | − | − | − | − | + | + | + | + |
| MS 223 | − | − | − | − | − | − | − | − | + | + | + | + |
| MS 246 | − | − | − | − | − | − | − | − | + | + | + | + |

+ both parallel assays positive (w = weak)
− both parallel assays negative
± one assay positive, one assay negative (ADH, LDC from nutrient agar positive for MS 246 and MS 219, VP from ethanol/agar positive for MS 75 to MS 246)
*positive in the Oxi/Ferm Tube Assay
oxidase assay (cytochromoxidase) in H2S and ONPG catalase assay with MAN, INO and SOR The test results in Table 4 again permit a classification of the individual strains into Groups I-III according to Table 3. However, small differences are observed within the groups:

MS 75 is able to liquify gelatin but MS 223 cannot
MS 219 and MS 246 may differ with respect to ADH and LDC (in addition, MS 246 has a tendency to flocculate during growth)

(c) Comparison of the two test systems (a) and (b)

The following cross-comparisons may be made respecting the five strains according to Table 1:

H2S formation, indole formation and arginine hydrolase are always negative in both systems. Urease is in relatively good accord in both assays and citrate utilisation is in complete accord in both assays. The different results in respect of N2 production (nitrate reduction) are explained by the greater sensitivity of the measurements in the API 20 E assay.

The results of the "Oxi/Ferm Tube" assay and of the "API 20 E" assay would permit the strains of Table 1 to be classified as Pseudomonas species, Pseudomonas-like species, Alcaligenes faecalis or Achromobacter species. Aside from biochemical characteristics, the nature of the flagellation of the gramnegative rods is typical for these genera. Accordingly, Pseudomonas strains have monotrichous or multitrichous polar flagellae and in very rare cases have no flagellae, while Achromobacter has 1 to 4, sometimes up to 8, peritrichous flagellae. An electron micrograph of a number of typical cells (see illustration above) shows, however, that the strains of Table 1 cannot be classified among any of the above mentioned genera. The strains are clearly appendaged bacteria. Both optical microscopy and electron microscopy show that the bacteria belong to the higher group of budding or appendaged bacteria and, within this group, to the genus Hyphomicrobium. The results of electron microscopy are in accord with the characteristics described for the genus Hyphomicrobium in Bergey's Manual of Determinative Bacteriology, 8th Edition, in the section entitled: "Budding and/or appendaged Bacteria".

PRESERVATION OF THE STRAINS

The following methods are suitable for preserving the strains of Table 1:

(a) adsorption of the cells of the respective strain onto glass beads in glycerol solution and subsequent storage at −20° C., (b) keeping the cells of the respective strain on slant agar, and (c) lyo-ampoules. The respective culture is centrifuged off from the nutrient solution and the biomass is resuspended in ¼ to ⅓ volumes of 15% skim milk and lyophilised.

The strains listed in Table 1 are able to form mutants spontaneously or to give rise to the artificial production of mutants, which mutants are also able, like the natural strains, to degrade lower alkanols, e.g. methanol or ethanol, lower alkanoates, e.g. sodium formate or sodium acetate, monosaccharides, e.g. glucose, disaccharides, e.g. saccharose, methylammonium compounds, e.g. methylammonium chloride, ethylmethylammonium chloride or dimethylammonium chloride, as well as in particular methyl sulfates, e.g. sodium methyl sulfate, in aqueous solution, and to produce biomass. Such mutants can be produced by chemical means, e.g. with certain guanine derivatives, e.g. N-methyl-N'-nitro-N-nitrosoguanidine, or with alkali nitrite, e.g. sodium nitrite, or by physical means, e.g. by ultraviolet, X-ray or radioactive radiation.

The microorganisms are used in a process for the microbiological purification of aqueous solutions by degradation of lower alkanols, lower alkanoates, monosaccharides, disaccharides, dimethyl phosphite, trimethyl phosphite, lower alkylammonium compounds, or of free amine bases thereof, or of methyl sulfate compounds as well as mixtures of these compounds, which process comprises culturing, in such an aqueous solution, a microorganism of the genus Hyphomicrobium or a mutant derived from said microorganism and suitable for the process, in the presence of nutrient inorganic salts and, if appropriate, of a nitrogen source, at about 20° C. to 40° C. and at a pH value of about 4 to 7.5, and, if desired, isolating the resultant biomass.

During the culturing or fermentation, the strains listed in Table 1 degrade the ingredients present in aqueous solution, e.g. in a wastewater, said ingredients being e.g. methanol, ethanol, glucose, sodium acetate, dimethyl phosphite, trimethyl phosphite, methylammonium chloride, dimethylammonium chloride or ethylmethylammonium chloride, and, in particular, sodium methyl sulfate, and consume oxygen.

The microorganisms listed in Table 1 are able to degrade these ingredients in some cases in very high concentrations of the compound or salt concerned. During the degradation, the microorganisms produce biomass and, further fermentation product, carbon dioxide. Ammonium chloride and hydrogen chloride are formed as additional fermentation products in the degradation of methylammonium chloride, dimethylammonium chloride or ethylammonium chloride, while sodium hydrogen sulfate is formed in the degradation of sodium methyl sulfate. The pH will be adjusted to values from about 4 to 7.5, preferably from about 5 to 6, by addition of a buffer solution e.g. phosphate buffer solution, or of an aqueous base, e.g. aqueous sodium or potassium hydroxide solution.

Fermentation is carried out in the presence of nutrient inorganic salts. Such salts are e.g. halides, e.g. chlorides, carbonates, sulfates or phosphates or alkali metals, alkaline earth metals or transition metals, as well as borates or molybdates of alkali metals.

Examples of preferred nutrient inorganic salts are disodium or dipotassium hydrogen phosphate, sodium or potassium dihydrogen phosphate, magnesium or iron sulfate, and potassium and calcium chloride. Zinc sulfate, manganese sulfate and copper sulfate, sodium molybdate and borax can additionally be added in small amounts.

For purifying aqueous solutions which do not contain nitrogen-containing compounds and contain e.g. only methanol, ethanol, glucose, dimethyl phosphite, trimethyl phosphite, formate, acetate or monoalkylsulfate ions, there are added as nitrogen source, e.g. amino acids, peptides or proteins or their degradation products such as peptone, or tryptone, meat extracts, flours, e.g. corn flour, wheat flour or bean flour, e.g. soybean flour, distillation residues of alcohol production, yeast extracts and, preferably, ammonium salts, e.g. ammonium chloride, or nitrates, e.g. potassium nitrate or ammonium nitrate.

Culturing is effected under aerobic conditions, e.g. with the introduction of oxygen or air and with shaking or stirring in shaking bottles or fermenters. Culturing can be effected in the temperature range from about 20° to 40° C., preferably from about 27° to 30° C.

Culturing can be carried out batchwise, e.g. by single or repeated addition of nutrient solution and of the corresponding sources of carbon and nitrogen; or continuously, by continuous addition of nutrient solution and of the corresponding sources of carbon and nitrogen.

It is preferred to effect culturing in several stages by first preparing one or more precultures, e.g. in a nutrient medium, with which precultures the main culture bath is then inoculated. A preculture may be prepared e.g. by inoculating a sterile solution, e.g. MV 7 containing a suitable nitrogen source, e.g. sodium methyl sulfate, with a sample of cells of the microorganism concerned, which is kept e.g. on slant agar, and incubating the batch for several days at 28° C. A fresh nutrient solution, e.g. MV 7 containing the same nitrogen source, is inoculated with this first preculture and the batch is incubated for several days at 28° C.

In order to monitor the course of the fermentation analytically, samples can be taken e.g. for measuring the pH of the culture or the optical density, which is a reference value for the growth of the strain in question, as well as for the gravimetric estimation on the basis of the dry weight of the biomass obtained.

Finally, the resultant biomass can be processed e.g. by one of the numerous methods described in European patent specification No. 0 010 243 and converted into fertiliser.

Biomass is defined in this context as comprising all cell systems in the living state, e.g. that of replication or resting, in the state of partial or complete death, or already in a state of enzymatic decomposition or of decomposition by foreign cultures, which cell systems are based on the microorganisms of this invention.

This biomass is a valuable raw material and can be used e.g. as single cell protein as cattle feed additive. The biomass can also be used as suspension or processed to fertiliser, e.g. after dehydration or pasteurisation. The biomass can also be used as starting material for the production of biogas with a high heat content (composition: about 70% of methane, 29% of carbon dioxide and 1% of hydrogen, heat content about 5500–6500 kcal/m$^3$), for example by anaerobic fermentation in fermentation towers. The residue (sludge) from the process for the production of biogas is also a high-grade fertiliser which, compared with the original biomass, is highly enriched with nitrogen.

The invention is illustrated by the following Examples.

EXAMPLE 1

(Preparation of the preculture)

1 sample of cells of the microorganism of strain MS 72 (see Table 1), which is kept on slant agar, is introduced into a shaking bottle containing 20 ml of MV 7 nutrient solution which has the composition as indicated above together with 5 g/l of sodium methyl sulfate. Then about 1 mmole of a phosphate buffer solution of pH 7 is added and the batch is incubated for 72 hours at 28° C. and 250 rpm. Then 5–7 mm of this first preculture are introduced into a second shaking bottle containing 100 ml of MV 7 nutrient solution, 10 g/l of sodium methyl sulfate and 5 mmoles of phosphate buffer of pH 7, and the batch is incubated for 72 hours at 28° C. and 250 rpm.

EXAMPLE 2

Precultures of the strains MS 75, 219, 223 and 246 (see Table 1), can be prepared as described in Example 1.

EXAMPLE 3

In a laboratory fermenter, 10 litres of optionally heat-sterilised MV 7 nutrient solution (sterilisation for 20 minutes at 120° C.) and sodium methyl sulfate solution which is optionally filtered under sterile conditions are combined to give an approximate total volume of 10 liters having a concentration of about 5 g/l of sodium methyl sulfate. A sample of about 500 ml of the second preculture of the strain MS 72 is added and the following conditions are maintained: pH 5.5, kept constant by adding, as required, 4N NaOH or 1N HC; temperature 28° C.; air supply 0.26 l/min; stirring rate 400–700 rpm.

The strain grows on pure sodium methyl sulfate as sole carbon source. The sodium methyl sulfate is almost completely degraded after 75 hours. The biomass obtained is in the form of a mixture of single cells or aggregates of different size which can be separated by sedimentation or centrifugation.

EXAMPLE 4

Sodium methyl sulfate can be degraded in aqueous solution as described in Example 3 by growing precultures of the strains MS 75, 219, 223 and 246 in a laboratory fermenter.

EXAMPLE 5

In a laboratory fermenter, 10 liters of heat-sterilised MV 7 nutrient solution (sterilisation for 20 minutes at 120° C.) are combined with a wastewater solution filtered under sterile conditions and containing sodium methyl sulfate (composition: 31% of sodium methyl sulfate, 10% of methanol, 1% of sulfate, 56% of water and less than 2% of aromatic compounds) so as to give a total volume of about 10 liters having a concentration of about 10 g/l of sodium methyl sulfate. A sample of about 500 ml of the second preculture of the strain MS 72 is added and the conditions described in Example 3 are kept. Degradation of the substrate is terminated after about 4–5 days.

EXAMPLE 6

Sodium methyl sulfate can be degraded in wastewater solutions filtered under sterile conditions in accordance with Example 5 by growing precultures of the strains MS 75, 219, 223 and 246 in a laboratory fermenter.

EXAMPLE 7

In the manner as described in Examples 5 and 6, sodium methyl sulfate can be degraded in wastewater solutions, omitting the filtration under sterile conditions, by cultivating the precultures of the strains MS 72, 75, 219, 223 and 246 in a laboratory fermenter.

What is claimed is:

1. A biologically pure culture of microorganisms of the genus Hyphomicrobium selected from the group of the following strains:

Hyphomicrobium NRRL-B-12573,
Hyphomicrobium NRRL-B-12572,
Hyphomicrobium NRRL-B-12571,
Hyphomicrobium NRRL-B-12570,
Hyphomicrobium NRRL-B-12569,
and mutants thereof.

2. A process for the microbiological purification of aqueous solutions by degradation of lower alkanols, lower alkanoates, monosaccharides, disacchardies, dimethyl phosphite, trimethyl phosphite, lower alkylammonium compounds or free amines thereof, or of methylsulfate compounds or mixtures thereof, which process comprises culturing in such aqueous solution a microorganism of the genus Hyphomicrobium according to claim 1 or a mutant derived from said microorganism suitable for the process, in the presence of nutrient inorganic salts and optionally of a nitrogen source, in the temperature range from about 20° to 40° C. and in a pH range from about 4 to 7.5, and, if desired, isolating the biomass obtained.

3. A process according to claim 2 for the microbiological purification of aqueous solutions by degradation of methanol, ethanol, glucose, dimethyl phosphite, trimethyl phosphite, methylammonium chloride, dimethylammonium chloride, ethylmethylammonium chloride or sodium methyl sulfate or mixtures of said compounds, which process comprises culturing in such aqueous solution a microorganism of the genus Hyphomicrobium according to claim 1 or a mutant derived from said microorganism which is suitable for the process.

4. A process according to claim 3 for the microbiological purification of aqueous solutions by degradation of sodium methyl sulfate, which process comprises culturing in such aqueous solution a microorganism of the genus Hyphomicrobium according to claim 1 or a mutant derived from said microorganism which is suitable for the process.

5. A process according to claim 2, wherein culturing the microorganism is carried out at 28° C.

6. A process according to claim 2, wherein culturing the microorganism is carried out batchwise.

7. A process according to claim 2, wherein culturing the microorganism is carried out continuously.

* * * * *